United States Patent [19]

Nichols

[11] Patent Number: 5,000,947

[45] Date of Patent: Mar. 19, 1991

[54] SHAPED ARTICLES CONTAINING LIQUEFIABLE POWDERS FOR DELIVERY OF COSMETIC AND OTHER PERSONAL CARE AGENTS

[75] Inventor: Larry D. Nichols, Arlington, Mass.

[73] Assignee: Moleculon, Inc., Elizabeth, N.J.

[21] Appl. No.: 358,690

[22] Filed: May 30, 1989

[51] Int. Cl.$^5$ .................. A61K 7/02; A61K 7/021; A61K 7/035; A61K 9/14

[52] U.S. Cl. .................. 424/69; 424/401; 424/65; 424/DIG. 5; 424/63; 424/59; 424/489

[58] Field of Search .......... 424/69, 65, 417, 418, 424/419, 484, 486, 488, 401, 489, DIG. 5, DIG. 10; 514/781

[56] References Cited

U.S. PATENT DOCUMENTS

| | | | |
|---|---|---|---|
| 2,891,946 | 5/1955 | Volberg et al. | 260/230 |
| 2,900,306 | 8/1959 | Slater | 167/90 |
| 3,640,741 | 2/1972 | Etes | 19/10 |
| 3,846,404 | 11/1974 | Nichols | 260/230 |
| 3,985,298 | 10/1976 | Nichols | 239/54 |
| 4,024,073 | 5/1977 | Shimizu et al. | 252/316 |
| 4,029,726 | 6/1977 | Nichols | 264/41 |
| 4,067,824 | 1/1978 | Teng et al. | 252/522 |
| 4,126,679 | 11/1978 | Davy et al. | 424/66 |
| 4,128,507 | 12/1978 | Mitzner | 252/522 |
| 4,193,989 | 3/1980 | Teng et al. | 424/60 |
| 4,252,789 | 2/1981 | Broad | 424/65 |
| 4,265,878 | 5/1981 | Keil | 424/68 |
| 4,268,498 | 5/1981 | Gedeon et al. | 424/59 |
| 4,280,994 | 7/1981 | Turney | 424/68 |
| 4,369,173 | 1/1983 | Causland et al. | 424/35 |
| 4,379,136 | 4/1983 | Mochida | 424/65 |
| 4,383,988 | 5/1983 | Teng et al. | 424/68 |
| 4,414,200 | 11/1983 | Murphy et al. | 424/63 |
| 4,440,742 | 4/1984 | Marschner | 424/65 |
| 4,504,465 | 3/1985 | Sampson et al. | 424/65 |
| 4,511,554 | 4/1985 | Geria et al. | 424/65 |
| 4,524,062 | 6/1985 | Laba et al. | 424/65 |
| 4,597,960 | 7/1986 | Cohen | 424/28 |
| 4,605,553 | 8/1986 | Passalacqua | 424/59 |
| 4,617,185 | 10/1986 | DiPietro | 424/65 |
| 4,643,856 | 2/1987 | Nichols | 264/41 |
| 4,659,571 | 4/1987 | Laba | 424/65 |
| 4,664,909 | 5/1987 | Marschner | 424/65 |
| 4,690,825 | 9/1987 | Won | 424/501 |
| 4,724,240 | 2/1988 | Abrutyn | 514/847 |
| 4,725,432 | 2/1988 | May | 424/66 |
| 4,731,243 | 3/1988 | Lindauer et al. | 424/65 |
| 4,743,444 | 5/1988 | McCall | 424/65 |
| 4,752,496 | 6/1988 | Fellows et al. | 427/27 |
| 4,755,433 | 7/1988 | Patel et al. | 428/422 |
| 4,759,924 | 7/1988 | Luebbe et al. | 424/42 |
| 4,781,917 | 11/1988 | Luebbe et al. | 424/65 |

*Primary Examiner*—Thurman K. Page
*Assistant Examiner*—Susan S. Rucker
*Attorney, Agent, or Firm*—Thomas J. Engellenner

[57] ABSTRACT

Shaped articles, such as cakes, sticks and other compacts, formulated with liquefiable powders containing various agents are disclosed for the delivery of cosmetic and other personal care products. In particular, microporous cellulosic powders, such as a cellulose triacetate (CTA), are disclosed as high liquid content vehicles for the active agents. The liquefiable powders can be compacted to form firm cakes or formulated with binders to yield sticks. The resulting shaped articles are neither oily nor gritty and yet permit the application of the cosmetic or personal care agents by simply rubbing or brushing the formulation onto the skin, in such a manner that the powder liquefies and appears to vanish. Shaped articles made in accordance with the present invention permit the delivery of high concentrations of active agents without the problems normally associated with liquids and oils.

44 Claims, No Drawings

SHAPED ARTICLES CONTAINING LIQUEFIABLE POWDERS FOR DELIVERY OF COSMETIC AND OTHER PERSONAL CARE AGENTS

BACKGROUND OF THE INVENTION

The technical field of this invention is cosmetic and personal care compositions and, in particular, the formulation of cakes, sticks and other shaped articles from cellulosic powders containing liquid payloads.

Fragrances and related products are typically formulated as oils or volatile solutions which are applied to the skin by hand or as aerosols. While such compositions, particularly oils, can achieve high payload concentrations, there are several disadvantages to the use of liquids. The containers are bulky and prone to breakage, spillage or leakage. Moreover, when fragrances are released as aerosols, there is considerable waste of the essential agents by dispersion and evaporation at the time of application.

Waxes and pastes have also been used for the delivery of perfumes and medications. Although these semiliquid vehicles may reduce spillage and evaporative losses, such vehicles are often less pleasing aesthetically because of their texture and oily appearance.

Another approach to the delivery of cosmetic and personal care products has been the formulation of such products as powders or cakes. Typically, the active agent is formulated with talc and/or cornstarch to create a powder Alternatively, a waxy binder can also be included and the resulting composition compressed into a cake, stick or other compact. Unfortunately, such powders and compacts have a limited capacity for retaining liquid agents without being reduced to a wet putty.

There exists a need for better compositions for delivery of cosmetic and personal care agents, such as colorants, perfumes, sunscreens, antiperspirants and medications, particularly in high concentrations and without the disadvantages of a liquid delivery vehicle.

SUMMARY OF THE INVENTION

Shaped articles, such as cakes, sticks and other compacts, formulated with liquefiable powders containing various agents are disclosed for the delivery of cosmetic and other personal care products. In particular, microporous cellulosic powders, such as cellulose triacetate (CTA), are disclosed as high liquid content vehicles for the active agents. The liquefiable powders can be compacted to form firm cakes or formulated with binders to yield sticks. The resulting shaped articles are neither oily nor gritty and yet permit the application of the cosmetic or personal care agents by simply rubbing or brushing the formulation onto the skin, in such a manner that the powder liquefies and appears to vanish. Shaped articles made in accordance with the present invention permit the delivery of high concentrations of active agents without the problems normally associated with liquids and oils.

As used herein, the term "personal care" agent includes cosmetics and other beneficial topical preparations. The term "cosmetic" is used to encompass fragrances, colorants, emollients, moisturizers and the like. More generally, the active agents which can be incorporated into liquefiable powders and formulated into shaped articles encompass any personal care composition which is liquid, soluble in a liquid, or otherwise dispersible within a liquid, including perfumes, blushes, eyeshadows, sunscreens, antiperspirants, moisturizers, lubricants, insect repellents, deodorants, analgesics, foot and acne preparations, and other skin medications.

In one aspect of the invention, it has been discovered that cellulosic powders containing liquid payloads of personal care products can be compacted to packing densities ranging from about 55 percent to about 75 percent, more preferably from about 60 percent to about 70 percent, of the void-free density of the combined materials to yield cakes that are dry and firm and yet readily permit transfer of the formulation to the skin by finger or brush. Such compacted cakes can be obtained by applying a pressure ranging from about 50 to about 80 PSI to a cellulosic powder which has been appropriately loaded with a liquid payload of the active agent. In the absence of other additives, the resulting shaped articles have a compacted density ranging from about 0.55 to about 0.75 gm/cc.

Powders and other forms of microporous cellulosic compounds, as well as the utility of such materials in the conveyance and delivery of liquid payloads, are described in the U.S. Pat. Nos. 3,846,404 and 3,985,298, herein incorporated by reference. Cellulosic powders and the like can be formed with liquid payloads by a coagulative technique, as described in U.S. Pat. No. 3,846,404 or, alternatively, by spraying using an evaporative technique.

In one technique, the liquefiable powders are formed by dissolving a cellulosic polymer and a pore-forming liquid in a volatile, polar solvent (e.g., a low molecular weight ester or diester) and then dispersively evaporating the solution, for example, by spray drying. Suitable volatile solvents for cellulosic polymers include methylene chloride, acetone, ethyl acetate, ethyl carbonate, methyl formate and the like. Methylene chloride is a preferred solvent when the cellulosic polymer is cellulose triacetate. Alternatively, other less volatile solvents, such as formic acid or the like, can be used and the resulting solution can be sprayed into a non-solvent such as methanol where the powder particles are then recovered by filtration and rinsing. The active agent can be incorporated into the solvent or introduced by liquid phase substitution after the powder is formed.

The cellulosic powders useful in the present invention can range from about one to about 500 microns in average diameter, preferably from about 5 to about 100 microns in average diameter, and typically are roughly microspherical in shape. They are further characterized by being microporous with interconnecting pores ranging in size from about 10 to about 5000 Angstroms and capable of holding liquid payloads of active agents. The cellulosic powder can be formed from cellulosic polymers chosen from the group of cellulose acetates, cellulose butyrates, cellulose nitrates, cellulose propionates, ethyl celluloses and discrete or molecular mixtures thereof. One preferred cellulosic powder is a polymeric powder of cellulose triacetate, having a (dry) acetyl content greater than about 42 percent. The liquid content of the cellulosic powders of the present invention can range from about 50 percent to about 95 percent by weight.

Compressing these soft, liquefiable powders would be expected to produce a weak, crumbly mass if the applied force were insufficient to expel liquid from the individual particles or a wet putty if the force were great enough to crush the particles and expel liquid. While crumbly or putty-like cakes can indeed be produced, it has been unexpectedly discovered that, under the proper conditions, the powders can be compressed into dry-looking, cohesive cakes from which visible powder can be picked up by a fingertip or soft applicator and, subsequently, liquefied on the skin. These shaped articles offer useful features beyond their visual and tactile novelty; they combine the advantages of three distinct physical forms in a single vehicle. Specifically, they provide (a) the portability and spill resistance of cakes, (b) the easy application and localization of powders, and (c) the concentration and invisibility of liquids.

The compacted powders of this invention are particularly useful as vehicles for fragrances. They are compatible with pure perfume oils and can readily carry concentrations of more than 50 percent by weight; other powder vehicles are limited to less than 20 percent liquid perfume. Since these powder cakes can approach the concentration of pure perfume oils, a cake of fragrant powder weighing only a few grams can provide a convenient small source of perfume for weeks of use. The high perfume concentration facilitates effective application, requiring only a touch of powder on a fingertip or applicator.

While frequent reference is made to the use of a fingertip to lift powder from a compacted cake to apply it to the skin, this task is also well served by other applicators, such as fiber or foam brushes or by woven, nonwoven or foam pads. Likewise, though perfumes and fragrances provide an important illustration of the utility of the liquefiable powder cakes of this invention, it is to be understood that these cakes are also of value for the conveyance and application to the skin of other cosmetic and skin care agents.

The powder cakes of this invention need not be composed solely of a liquefiable powder. Additives may be blended with the liquefiable powder to improve the appearance or mechanical properties of the cake or to provide some unconfined active ingredient not incorporated into the powder particles. For example, a low-melting point, micronized wax can be blended with a liquefiable powder and then formed into a cake; brief warming then causes the wax to melt and resolidify, acting as a binder and strengthening the cake. Pigments, bronze or aluminum powders, or pearlescent agents, such as mica, can be included to provide color, metallic reflection or sparkle. Such visual additives may he used to change the appearance of the cake or the skin or both. Other examples of additives include the addition of aluminum chlorhydrate as an anti-perspirant or the addition of talc or cornstarch to produce a drier, smoother texture.

Cakes made by blending other powders with these liquefiable powders can retain both the ability to deliver soft powder to a finger or applicator and the ability of that powder to liquefy and vanish when subsequently rubbed on the skin. Blendinq can be a preferred method for formulating with materials which are insoluble in the spray solvent or which lose their desirable appearance or activity when incorporated directly into the powder particles.

In another aspect of this invention, the methods used to form compacted cakes of liquefiable powder can be adapted to prepare other shaped forms and, in particular, to produce stick products for cosmetic or dermal applications. Sticks made from compacted liquefiable powders can combine useful levels of strength, comfort and softness, as well as high payload concentrations. This makes possible new concentrated stick products which are non-greasy and hypo-irritating. Applications for sticks include, but are not limited to, deodorants, antiperspirants, perfumes, cosmetics, sunscreens, insect repellents and skin medications.

Sticks incorporating liquefiable powders with active agent payloads can be made by a variety of techniques. For example, sticks can be formulated by compounding a liquefiable powder with fatty alcohols, fatty acids, and/or salts of fatty acid anions with metallic or alkanolamine cations to produce a stick having a soap as the binding agent.

Alternatively, stick compositions can be formed by compounding a liquefiable powder with soft water-soluble polymers, such as polyethylene or polypropylene glycols, to produce a stick having a soluble wax as the binding agent. Sticks can also be made up by compounding a liquefiable powder with silicones or with blends of liquids and solids, such micronized aluminum antiperspirant salts and/or propylene glycols, to produce sticks having a thick or partially solidified slurry as the binding agent. In yet another approach, sticks can be formed by compounding a liquefiable powder with a fusible wax, such as myristyl myristate, and then applying heat and pressure to produce sticks having a fatty ester wax as the binding agent.

The above binding agents can be introduced directly, or as payload in a second portion of liquefiable powder to be blended with that carrying the active ingredient. Other methods of stick production will readily occur to those skilled in the art.

The invention will next be described in connection with certain exemplary methods and compositions. However, it should be clear that various additions, subtractions and changes can be made by those skilled in the art without departing from the spirit or scope of the invention.

DETAILED DESCRIPTION

The examples below illustrate the preparation of liquefiable powders, their conversion into cakes, the use of diverse active ingredients and additives and the preparation of other shaped forms. Fragrance "A" in these examples is a highly concentrated test fragrance composed of 20.5 percent Adol-66, 6.9 percent DC-200 Dimethicone, 20.6 percent DC-345 Cyclomethicone and 52.0 percent Firmenich Fragrance Oil 423.236/B.

EXAMPLE 1

15 gm of CTA was dissolved in 900 gm of methylene chloride by moderate stirring for 1 hour. 85 gm of fragrance "A" was added to the resulting clear solution and stirred until fully dispersed. This solution was sprayed at 1000 PSI from a 0.0135" nozzle downward into a tower 100 cm in diameter and 300 cm tall through which 1250 liters per minute of solvent-free air was passing from top to bottom.

The resulting evaporatively-formed, liquid-containing CTA powder was collected on a fabric filter spanning the bottom of the tower, and the solvent-laden air was passed through carbon beds to collect solvent vapors.

The product was transferred from the filter into a steel tray and left exposed as a 1 cm layer in a ventilated hood for 15 minutes to remove residual solvent. Analysis showed 85.2 percent fragrance and 14.8 percent CTA, with less than 1 ppm of methylene chloride.

A 5 mg sample of this powder placed on the inner left wrist and rubbed gently with the right forefinger was readily distributed over an area of about 3 square centimeters and then completely vanished on further gentle rubbing. Fragrance imparted to the treated skin area persisted until washed after six hours.

No grittiness was observed during this experiment; the mean particle diameter was about 30 microns, and particles larger than 150 microns were not observed. This evaporative process produced smaller particles than the coagulative process (of Example 2 below) for at least two reasons: the lower viscosity of the methylene chloride solution promoted breakup of the spray into smaller initial droplets, and the evaporation of the methylene chloride from these droplets led to further reduction in diameter.

EXAMPLE 2

Liquefiable powders were also prepared according to the method described in U.S. Pat. No. 3,846,404. 4.5 percent by weight of CTA was dissolved in formic acid by slow stirring overnight. This solution was pumped at 1000 PSI through a 0.0135" nozzle directed downward into a pool of methanol 100 cm in diameter and 10 cm deep, located 100 cm below the nozzle. Approximately 1 kg of polymer solution was sprayed, and the resulting coagulated powder was collected from suspension using a bag filter. Without ever being taken to dryness, the collected slurry was rinsed with methanol and then with water until the effluent pH was above 5.0.

A portion of the rinsed slurry was diluted with water to a total weight of 201 gm, mixed until uniform, and a 1 gm aliquot taken and analyzed to contain 1.02 percent CTA. Thus, the remaining 200 gm of slurry contained 2.04 gm of CTA. Past experience teaches that this method of production produces coagulated CTA particles composed internally of 8 percent CTA and 92 percent water, so the slurry was calculated to contain 25.5 gm of water-loaded CTA powder.

Successive rinses with methanol and ether provided a thick slurry of about 25.5 gm of powder in about 50 cc of ether. To this was added 23.5 gm of fragrance "A". After gentle mixing, the resulting slurry was spread in a large, stainless steel tray and placed in a ventilated hood. A layer of paper placed loosely over the tray retarded the initial evaporation rate, avoiding condensation of moisture in the powder and insuring against the buildup of an explosive atmosphere in the passing airstream.

When small cracks began to appear, the powder was gently loosened with a spatula to break up incipient lumps. Another hour of ventilation in the uncovered tray produced 24.9 gm of liquefiable powder analyzed to contain 92.3 percent fragrance and 7.7 percent CTA.

A 5 mg sample of this powder placed on the inner left wrist and rubbed gently with the right forefinger was readily distributed over an area of about 3 square centimeters; it readily disappeared when gently rubbed with the same fingertip. Fragrance imparted to the treated skin again persisted until the area was washed after six hours. A slight grittiness was observed during application to the skin. Although the mean particle diameter was about 60 microns, occasional particles larger than 150 microns existed and could be felt as grit.

Other than grittiness, which was observed when these liquefiable powders were prepared by coagulation, the products of coagulative and evaporative spraying appeared to be very similar. They were both white, free-flowing powders with only a slight tendency to form loose aggregates. They both could contain 85 percent to 95 percent fragrance, they both spread easily on the skin, and they both liquefied and vanished when rubbed.

EXAMPLE 3

Experiments were conducted in which the liquefiable powder of Example 1 was compressed into small steel pans of a type commonly used commercially for eye shadows and blushes. Each pan was about 3 mm deep, 26 mm wide and 32 mm long with slightly rounded ends; the flush-filled volume was 2.5 cc.

Two methods of compression were employed. In the first, a pan was slightly overfilled with loose powder and then pressed flush with a flat aluminum block. More powder was spread smoothly on top of the pressed cake and, again, pressed flush. This process was repeated until the desired load weight was obtained.

The second method of fill used circular 35 mm diameter plastic petri dishes as an aid to filling. A measured weight of powder was placed in the dish and uniformly distributed over the circular area. A steel pan was then pressed face down into the powder layer until it butted against the base of the petri dish. The pan was removed from the dish and the surface of the pressed cake dressed by compression against a smooth aluminum block.

When similar weights of powder were compressed into similar pans by these two methods, the properties of the cakes so produced were indistinguishable. The second method proved simpler and more rapid and was, therefore, employed for cake compression in these examples.

The powder of Example 1, loosely flush-loaded into steel pans, was found to weigh about 0.50 gm per pan, corresponding to a loose density of 0.20 gm/cc. The powder was then compacted into pans at weights of 1.25, 1.35 and 1.50, 1.625, 1.75, 1,875 and 2.00 grams, corresponding to packed densities of 0.50, 0.55 0.60, 0.65, 0.70, 0.75 and 0.80 gm/cc.

The 0.50 gm/cc cakes were very fragile. Contact with a moving fingertip tended to gouge the surface, and lightly tapping the bottom of an inverted pan 10cm above a hard surface caused the cake to fall out and shatter. Gentle manipulation of the cake fragments readily reverted them to loose powder.

The 0.80 gm/cc cakes were firm, oily to the touch and slightly darker than the lower density cakes. Gentle fingertip-rubbing produced no visible transfer of powder from cake to finger, though fragrance and oil were detectable on the finger. Heavier rubbing transferred a putty-like mass of material to the fingertip. This could be spread on the skin like a lotion but lacked perceptible powdery qualities. Tapping an inverted pan did not readily dislodge the cake; but a spatula could be used to pry a cake from its pan. The freed cake, which was oily and slightly flexible, could be crumbled into smaller fragments but would not revert to a loose powder.

The intermediate cakes with packed densities ranging from 0.55 to 0.75 gm/cc looked dry, like the low density (0.50 gm/cc) cake. Rubbed with a fingertip, they transferred a small but visible coating of powder to the finger. When that powder was rubbed on the inner wrist, it was visible at first but vanished when rubbed for a few more seconds. Tapping of an inverted pan 10 cm above a tabletop did not readily dislodge the cake; but with persistent and vigorous tapping, it was possible to cause most of the cake to fall out. Typically, there was little fragmentation due to impact with the table, and the dislodged cake could be carefully picked up in one piece. When portions of the cake were broken off, they reverted on gentle manipulation to a free powder, similar to the starting material. The properties of these cakes ranging in packing density from about 0.55 gm/cc to about 0.75 gm/cc corresponded closely to those desired for a commercial caked powder product.

EXAMPLE 4

The coagulative powder of Example 2 was loaded into the steel pans of Example 3 to a density of 0.65 gm/cc. The properties of the resulting cakes of coagulative powder were indistinguishable from those of evaporative powder cakes of the same density.

EXAMPLE 5

The experiments of Example 3 were repeated with a liquefiable powder made by the method of Example 1 but containing mineral oil in place of fragrance "A". Although the loose density of this powder in the pans was measured to be 0.3 gm/cc, 50 percent denser than that in Example 3, the best cakes were again found to correspond to a packed density of about 0.55 gm/cc to about 0.75 gm/cc. Thus, the properties of liquefiable powder cakes appear to depend more on the absolute packing density than on the ratio of final, packed density to the initial, loose density.

EXAMPLE 6

The above example shows that packing of these liquefiable powders into cakes can be controlled by weight and volume. Experiments were conducted to determine whether applied pressure is also a practical method of control. The receptacles were plastic compacts, having a smooth-walled cavity 44 mm in diameter and a flush-filled volume of 15 cc. An aluminum cylinder was machined with a smooth face and a loose fitting diameter of 44 mm. The cavity was filled with the powder of Example 1, the cylinder placed on top and a known force applied to the cylinder to compress the powder. The cylinder was then removed, and the resulting compacted cake examined by eye, touch, transfer and dislodgment. The best cakes were obtained at forces between 130 and 160 pounds, corresponding to pressures between 55 and 70 PSI. The packed density of these cakes was between 0.65 and 0.70 gm/cc, in excellent agreement with the results obtained in Example 3.

EXAMPLE 7

Cakes similar to the 0.65 g/cc cakes of Example 3 were prepared using fragrance "A" powder mixed with 10 percent by weight of a cosmetic blend of mica and titania (Mearl Corporation, TIMICA Extra Large Sparkle 110S). The resulting cakes showed good coherence and transfer, together with an attractive pearlescent sparkle. Coherence was assessed by repeatedly dropping a filled pan bottom-down onto a flat slab from a height of 12"; 5 to 10 drops were needed to cause the powder cake to crack and dislodge from the pan. Transfer to a a fingertip was measured from one cake 280 times and was found to average about 2.0 mg per transfer throughout the test.

More heavily pigmented cakes were prepared using liquefiable powder made as in Example 1 but containing 92 percent of mineral oil. 67 percent by weight of this powder was blended with 30 percent venetian red powdered iron oxide pigment and 3 percent TIMICA 110S. Good cake properties were obtained at packed densities of about 0.90 gm/cc, higher than before because of the high density of the iron oxide pigment (about 5.2 gm/cc). Corrected for density, this packing is in good agreement with the 0.65 g/cc values for powders of normal density. Even at this high level of admixed pigment, transfer from cake to fingertip remained good, and the transferred powder rubbed out smoothly onto the skin, leaving no visible powdery residue. There was visible pigmentation of the skin by the venetian red. A caked, liquefiable powder of this type would find utility as a blush or eye shadow.

These experiments show that the unique properties of the liquefiable powder cakes can remain unimpaired by admixture with as much as 33 percent of pigments and fine powders.

EXAMPLE 8

The powder of Example 1 was blended with 10 percent by weight of a finely powdered polyethylene glycol (PEG 8000, melting point 60 C) and compacted into a cake in a small, steel pan, following the method of Example 3. The resulting cake, in its pan, was placed in a sealed bottle to prevent excessive loss of volatiles and heated to 70° C. for 20 minutes and then cooled and examined. There was no apparent change in appearance or fragrance. Pried from the tray with a spatula, the cake remained in one piece when dropped 10 cm onto a hard surface. It was possible to break the cake into smaller pieces, but it resisted attempts to crumble it back into powder form. This illustrates that fusible additives can be employed to strengthen the powder cakes in this invention.

EXAMPLE 9

The evaporative spray method of Example 1 was used to prepare samples of liquefiable powder having the following compositions by weight:

| | | |
|---|---|---|
| (a) | CTA | 15.2% |
| | PABA | 5.1% |
| | DC 344 Silicone | 33.9% |
| | DC 345 Silicone | 24.6% |
| | Finsolv TN | 12.7% |
| | Diisopropyl Adipate | 8.5% |
| (b) | CTA | 16.2% |
| | Diethyltoluamide | 42.0% |
| | DC 344 Silicone | 41.8% |
| (c) | CTA | 16.8% |
| | Dimethylisosorbide | 26.7% |
| | Diisopropyl Adipate | 54.5% |
| | Benzoyl Peroxide | 2.0% |

These formulations constituted a sunscreen, an insect repellent and an anti-acne powder, respectively. All three showed typical, liquefiable powder behavior, resembling a white powder and vanishing into an imperceptible liquid film when rubbed gently on the skin.

The petri dish method of Example 3 was used to compact these powders to a density near 0.65 gm/cc in small steel pans. All formed cohesive cakes, all delivered visible powder when rubbed with a fingertip, and the delivered powders all vanished when rubbed gently on the skin. Thus, these powders of diverse utility and composition are all suitable for conversion into the liquefiable powder cakes of this invention.

EXAMPLE 10

A liquefiable powder containing 84.8 weight percent DC 345 silicone liquid was prepared by the method of Example 1. 66 parts of this powder were mixed with 24 parts of micronized aluminum chlorhydrate, a common antiperspirant, and 10 parts of finely powdered PEG 8000, a hard, non-oily polyethylene glycol melting at 60° C. The three powders were blended by vigorous vortexing at a rate sufficient to fluidize the mass of powder. 30 grams of this mixture was compacted into a cylindrical polypropylene centrifuge tube to a volume of 45 cc by adding portions weighing 2 to 4 grams and pressing with a loosely fitting polyethylene cylinder to a density of about 0.65 gm/cc after each addition. The compacted mass, sealed in its outer tube, was warmed in an oven to 75° C. for 25 minutes to fuse the PEG. Slight shrinkage occurred, and the stick separated from the walls of the tube so that it could be removed.

What is claimed is:

1. A shaped article for delivery of a personal care agent, the shaped article comprising a compacted formulation of a liquefiable, cellulosic powder, the liquid content of the powder ranging from about 50 percent to about 95 percent liquid and containing a personal care agent, the article being compacted to provide a firm cake having a packed density ranging from about 55 percent to about 75 percent of its void-free density.

2. The shaped article of claim 1 wherein the cellulosic powder is a polymeric powder chosen from the group consisting of cellulose acetates, cellulose butyrates, cellulose nitrates, cellulose propionates, ethyl celluloses and discrete and molecular mixtures thereof.

3. The shaped article of claim 1 wherein the cellulosic powder is a cellulose triacetate polymeric powder.

4. The shaped article of claim 1 wherein the powder further comprises particles ranging in average diameter from about 1 to about 500 microns.

5. The shaped article of claim 1 wherein the powder further comprises particles ranging in average diameter from about 5 to about 100 microns.

6. The shaped article of claim 1 wherein the powder of the compacted formulation has a packed density ranging from about 60 percent to about 70 percent of its void-free density.

7. The shaped article of claim 1 wherein the powder of the compacted formulation has a packed density, ranging from about 0.55 to about 0.75 gm/cc.

8. The shaped article of claim 1 wherein the personal care agent is a liquid comprising at least one topical preparation chosen from the group consisting of fragrances, colorants, emollients, skin moisturizers, lubricants, sunscreens, deodorants, analgesics, antiperspirants, insect repellents, foot treatments, acne treatments, medications and mixtures thereof.

9. The shaped article of claim 1 wherein the personal care agent is a cosmetic.

10. The shaped article of claim 1 wherein the compacted formulation further includes at least one additive not incorporated within the liquefiable powder.

11. The shaped article of claim 10 wherein the additive is a colorant.

12. The shaped article of claim 10 wherein the additive is a pearlescent agent.

13. The shaped article of claim 10 wherein the additive is a binder.

14. The shaped article of claim 10 wherein the additive is a fusible wax.

15. The shaped article of claim 10 wherein the additive is a talc.

16. The shaped article of claim 10 wherein the additive is a mica.

17. The shaped article of claim 10 wherein the additive is a soap.

18. The shaped article of claim 10 wherein the additive is a water soluble polymer.

19. The shaped article of claim 10 wherein the additive is a polyglycol.

20. The shaped article of claim 10 wherein the additive is an antiperspirant salt.

21. A method of formulating shaped articles for topical delivery of a personal care agent, the method comprising:
    preparing a solution comprising a cellulosic polymer in a volatile solvent, and a miscible pore-forming liquid;
    forming a liquefiable powder from said solution by elimination of said solvent, said powder comprising microporous polymeric particles impregnated with a liquid phase carrying at least one personal care agent, said personal care agent being introduced either into the pore-forming liquid prior to powder formation or by substitution of a liquid phase containing the personal care agent for an initial liquid phase after powder formation; and
    compacting said powder by application of pressure to yield a firm cake having a packed density ranging from about 55 percent to about 75 percent of its void-free density.

22. The method of claim 21 wherein the step of preparing a solution further includes preparing a solution comprising a cellulosic polymer chosen from the group selected from cellulose acetates, a cellulose butyrates, cellulose nitrates, cellulose propionates, ethyl celluloses and discrete or molecular mixture.

23. The method of claim 21 wherein the step of preparing a solution further includes preparing a solution comprising cellulose triacetate.

24. The method of claim 21 wherein the step of preparing a solution further includes dissolving or suspending a personal care agent in said solution.

25. The method of claim 21 wherein the step of forming a powder further includes forming a powder by evaporation of said solution.

26. The method of claim 21 wherein the powder is formed by spraying.

27. The method of claim 21 wherein the step of forming the powder further includes substituting a liquid phase containing at least one personal care agent for the initial liquid phase.

28. The method of claim 21 wherein the powder is formed by spray immersion of said solution into a nonsolvent followed by rinsing to remove solvent residues and collection of the powder by filtration.

29. The method of claim 28 wherein the step of forming a powder further includes substituting a liquid phase containing at least one personal care agent for the initial liquid phase.

30. The method of claim 21 wherein the step of compacting said powder further includes compacting said powder by a pressure ranging from about 50 to about 80 PSI.

31. The method of claim 21 wherein the step of compacting said powder further includes compacting said powder to a packing density ranging from about 60 percent to about 70 percent of its void-free density.

32. The method of claim 21 wherein the step of compacting said powder further includes compacting said powder to a packing density in the absence of additives ranging from about 0.55 to about 0.75 gm/cc.

33. The method of claim 21 wherein the method further comprises blending said liquefiable powder with at least one additive not incorporated in the liquefiable powder.

34. The method of claim 33 wherein the additive is chosen from the group consisting of colorants, pearlescent agents, binders, fusible waxes, talc, mica, soap, water-soluble polymers, silicones, glycols, and antiperspirant salts.

35. A shaped article for delivery of a personal care agent, the shaped article comprising a formulation of a liquefiable, cellulosic powder, the liquid content of the powder ranging from about 50 percent to about 75 percent and containing a personal care agent and a binding agent, the article being formed by compaction to provide a solidified stick having a packed density ranging from about 55 percent to about 75 percent of its void-free density.

36. The shaped article of claim 35 wherein the cellulosic powder is a polymeric powder chosen from the group consisting of cellulose acetates, cellulose butyrates, cellulose nitrates, cellulose propionates, ethyl celluloses and discrete and molecular mixtures thereof.

37. The shaped article of claim 35 wherein the cellulosic powder is a cellulose triacetate polymeric powder.

38. The shaped article of claim 35 wherein the powder further comprises particles ranging in average diameter from about 1 to about 500 microns.

39. The shaped article of claim 35 wherein the powder further comprises particles ranging in average diameter from about 5 to about 150 microns.

40. The shaped article of claim 35 wherein the personal care agent is a liquid comprising at least one topical preparation chosen from the group consisting of fragrances, colorants, emollients, skin moisturizers, lubricants, sunscreens, deodorants, analgesics, antiperspirants, insect repellents, foot treatments, acne treatments, medications and mixtures thereof.

41. The shaped article of claim 35 wherein the binding agent is an agent chosen from the group consisting of soaps, gels, polyglycols, silicones, and waxes.

42. A method of formulating shaped articles for topical delivery of a personal care agent, the method comprising:
preparing a solution comprising a cellulosic polymer in a volatile solvent, and a miscible pore-forming liquid;
forming a liquefiable powder from said solution by elimination of said solvent, said powder comprising microporous polymeric particles impregnated with a liquid phase carrying at least one personal care agent, said personal care agent being introduced either into the pore-forming liquid prior to powder formation or by substitution of a liquid phase containing the personal care agent for an initial liquid phase after powder formation;
compounding the liquefiable, cellulosic powder containing a personal care agent with a binding agent; and
shaping the resulting formulation by application of pressure to yield a stick having a packed density ranging from about 55 percent to about 75 percent of its void-free density.

43. The method of claim 42 wherein the personal care agent is a liquid comprising at least one topical preparation chosen from the group consisting of fragrances, colorants, emollients, skin moisturizers, lubricants, sunscreens, deodorants, analgesics, antiperspirants, insect repellents, foot treatments, acne treatments, medications and mixtures thereof.

44. The method of claim 42 wherein the binding agent is an agent chosen from the group consisting of soaps, gels, polyglycols, silicones, and waxes.

* * * * *